United States Patent [19]

Hill et al.

[11] 4,337,166
[45] Jun. 29, 1982

[54] COMPOSITIONS FOR TREATING HAIR AND OTHER FIBROUS MATERIALS

[75] Inventors: Michael P. L. Hill, St. Lythans; Petrina F. Fridd, Penarth, both of Wales

[73] Assignee: Dow Corning Limited, Barry, Wales

[21] Appl. No.: 255,188

[22] Filed: Apr. 17, 1981

[30] Foreign Application Priority Data

Apr. 19, 1980 [GB] United Kingdom ................. 8012933

[51] Int. Cl.$^3$ ............................................. C11D 17/00
[52] U.S. Cl. ................................. 252/174.15; 424/70; 252/174.21; 252/DIG. 13; 252/550
[58] Field of Search ..................... 424/70; 252/174.15, 252/174.21, DIG. 13, 550

[56] References Cited

U.S. PATENT DOCUMENTS 2,826,551 3/1958 Green ............................. 252/174.15
3,964,500 6/1976 Drakoff ................................ 424/70
4,006,176 2/1977 Heckert et al. ................. 252/174.15

Primary Examiner—Shrive P. Beck
Attorney, Agent, or Firm—George A. Grindahl; W. J. Walbeoff

[57] ABSTRACT

A detergent composition, particularly for use as a hair shampoo, consisting of a detergent substance, for example one based on a fatty alcohol or a fatty alcohol ethoxylate, and from 0.5 to 20 percent by weight, based on the total composition, of a cyclic methyl siloxane.

The presence of the cyclic siloxane results in reduced drying time of the washed fibres.

6 Claims, No Drawings

COMPOSITIONS FOR TREATING HAIR AND OTHER FIBROUS MATERIALS

This invention relates to compositions for use as shampoos for hair and other fibrous materials.

It is known to employ certain silicones as additives to hair treating compositions such as hair conditioning agents. It has also been disclosed in U.S. Pat. No. 2,826,551 that the addition of a liquid linear polysiloxane to a hair shampoo results in the treated hair having a reduced tendency to tangle. The operative liquid linear silicones are stated therein to be non-volatile under normal use conditions and to have a preferred viscosity of at least 100 cS at 25° C. Further disclosure of the addition of silicones to hair shampoos occurs in U.K. Patent Specification No. 849,433 which discloses that polymerised dimethyl and diethyl silanediols having viscosities within the range from 1.0 to 2,500,000 centistokes may be incorporated into detergent compositions. The said specification states that use of the detergent compositions as hair washing preparations decreases the length of time required to dry the hair after shampooing. However, according to tests that we have carried out, the decrease in drying time obtained with the described polymerised diols, e.g. those having viscosities of about 300 cS, is relatively small. There has therefore remained a need for a hair washing preparation having a significantly reduced drying time following the shampooing step.

According to this invention there is provided a detergent composition which is particularly adapted to the washing of hair and other natural and/or synthetic fibrous materials, the said composition comprising one or more detergent substances and from 0.5 to 20% by weight, based on the total weight of the composition, of at least one cyclic siloxane represented by the general formula

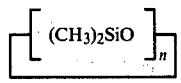

in which n has a value of from 3 to 6 inclusive.

The detergent substance employed in the compositions of this invention may be any of those which find application in the shampooing of hair and other fibrous materials. Such detergent substances include the fatty acid soaps, alkyl benzene sulphonates, alkyl sulphates, alkyl ether sulphates, monoglyceride sulphates, alkyl phosphates, methyl taurides and the fatty acid alkanolamides. When the detergent composition is intended for use as a shampoo for the hair of humans or animals the preferred detergent substances are those based on fatty alcohols or fatty alcohol ethoxylates, particularly those derived from lauryl and myristyl alcohol, and their salts, for example sodium lauryl sulphate, sodium lauryl ether sulphate, ammonium lauryl sulphate, triethanolamine lauryl sulphate, monoethanolamine lauryl sulphate, disodium lauryl ethoxy sulphosuccinate and disodium cocomonoethanolamide ethoxy sulphosuccinate. The concentration of the detergent component in the composition can vary widely depending on the type of shampoo product required. For most conventional shampoo applications, however, the detergent is normally present in the end-product in a proportion of from 7.5% to 50% (preferably 10–25%) by weight, the remainder being water and other additives such as foam stabilisers, preservatives and perfumes.

The siloxane component of the compositions of this invention comprises one or more cyclic siloxanes which can be represented by the general formula set out hereinabove. Specifically, the cyclic siloxanes are respectively hexamethylcyclotrisiloxane, octamethylcyclotetrasiloxane, decamethylcyclopentasiloxane and dodecamethylcyclohexasiloxane. Compared with the linear polydimethylsiloxanes the cyclic siloxanes employed according to this invention are relatively volatile materials having boiling points below about 250° C. at 760 mm Hg. The cyclic siloxanes may be employed as the individual compounds or as mixtures of two, three, or all four. The trisiloxane in its pure form is a solid at just below normal room temperature. It is therefore preferred that it be employed as a mixture with a higher cyclic siloxane, for example the tetrasiloxane or pentasiloxane or both.

From 0.5 to 20% by weight of the cyclic siloxane is employed to prepare the compositions of this invention, the preferred proportion being from about 2% to 10% by weight, based on the total weight of the composition. Dispersion of the cyclic siloxane in the shampoo composition can be achieved by any convenient procedure, for example by adding the siloxane per se to the finished shampoo composition with vigorous stirring. More preferably however the siloxane is emulsified prior to incorporation into the composition.

In addition to the two essential ingredients the compositions of this invention may contain other substances generally present in detergent compositions. For example, the composition may be thickened if desired by the addition of known viscosity increasing agents such as sodium chloride, cetyl alcohol, linoleic diethanolamide and cellulosic thickeners such as hydroxyethyl cellulose. Foam stabilising agents may also be incorporated, examples of such agents being coconut diethanolamide, lauric isopropanolamide, alkyl dimethyl betaine, alkyl dimethyl amine oxide and silicone-glycol copolymers. Additional ingredients which may normally be present include preservatives, such as formalin, pearlising agents, stearates and waxes, pH modifiers, colorants and perfumes. Conventional conditioning agents may also be incorporated. However, the cyclic siloxanes themselves are effective hair conditioning agents and it has been found that hair which has been shampooed with the compositions of this invention generally possesses gloss and ease of combing.

The following examples, in which the parts are expressed by weight, illustrate the invention:

EXAMPLE 1

A mixture of cyclic methyl siloxanes consisting of about 70% by weight of decamethylcyclopentasiloxane and about 25% by weight of dodecamethylcyclohexasiloxane, the remainder being the cyclotetra- and cyclotri-siloxanes, was emulsified in its own weight of water employing a non-ionic emulsifying agent. Two parts of the emulsion was then incorporated with vigorous stirring into eight parts of a hair shampoo (sold by Boots under the name Rosemary and believed to contain a fatty alcohol- or fatty alcohol ethoxylate-derived detergent) to give a detergent composition (Composition A) according to this invention.

Composition A and a control composition (no siloxane) were employed to shampoo switches of human hair, each approximately 30 cm in length and weighing 30 g. Each switch was shampooed by immersion in water at 30° C. containing 4% by weight of the detergent composition. After immersion for about 10 seconds the switch was removed and rubbed between the hands for about 20 seconds. This wash procedure was performed three times and the switch finally rinsed free of suds. Excess rinse water was squeezed manually from the switch which was then weighed and dried by gentle heat from a warm air source. Further weighings were performed during the drying period. From graphs of the results the times required for the switches to lose 25, 50, 75 and 90% by weight of their immediate post wash water content were ascertained.

The above described procedure was repeated except that instead of the cyclic siloxanes there was added an equal proportion of a trimethylsiloxy-terminated polydimethylsiloxane having a viscosity of 100 cS at 25%C. The composition was designated Composition B and its control (no siloxane) was designated Control B.

The results obtained for Compositions A and B and the controls were as follows:

| % Water Lost | Time (min.) | | | |
|---|---|---|---|---|
| | Composition A | Control A | Composition B | Control B |
| 0 | 0 | 0 | 0 | 0 |
| 25 | 5 | 8 | 9 | 12 |
| 50 | 11 | 14 | 21 | 28 |
| 75 | 21 | 29 | 45 | 57 |
| 90 | 38 | 55 | 65 | 71 |

EXAMPLE 2

The procedure of Example 1 was repeated except that as the cyclic siloxane there was employed a mixture containing about 84% by weight of octamethylcyclotetrasiloxane and about 16% by weight of decamethylcyclopentasiloxane. Hair washed with the shampoo containing the cyclic siloxane dried more quickly than hair washed with the same shampoo to which no siloxane had been added or to which 100 cS polydimethylsiloxane had been added in place of the cyclic siloxane.

EXAMPLE 3

A pearlised shampoo composition was prepared by mixing:

| | |
|---|---|
| sodium lauryl ether sulphate (28% solution in water) | 40 parts |
| pearlising agent (Empicol 0627) | 8 parts |
| coconut diethanolamide | 3 parts |
| thickening agent | qs |
| citric acid | to pH 6.5–7.0 |
| water | balance to 100 parts |

To the shampoo composition (9 parts) was added, with stirring, the emulsified mixture (1 part) of cyclic siloxanes employed in Example 1. The resulting composition was then used to shampoo switches of human hair (30 g) each being washed twice for a period of about 20 seconds with a 20% by weight solution of the shampoo in water (45° C.). The hair was rinsed in warm water after each wash.

Following the second rinse excess water was squeezed out manually, the switches were weighed and then placed in a current of warm air (about 70° C.) until dry. The loss of weight was monitored periodically during drying and the data employed to determine the times required for the switches to lose 25, 50, 75 and 90% by weight of their immediate post wash water content. The procedure was repeated using a control shampoo (no siloxane) and the times recorded for the siloxane-modified shampoo were expressed as a percentage of the corresponding drying times for the control. At all stages of water loss the use of the siloxane-modified shampoo resulted in a shorter drying time than the control, as follows:

| % weight of water lost | % time required versus control |
|---|---|
| 25 | 71.8 |
| 50 | 73.4 |
| 75 | 80.3 |
| 90 | 80.5 |

That which is claimed is:

1. A liquid detergent composition consisting essentially of one or more detergent substances and from 0.5 to 20 percent by weight, based on the total weight of the composition, of at least one cyclic siloxane represented by the general formula

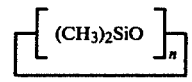

in which n has a value of from 3 to 6 inclusive.

2. A composition as claimed in claim 1 wherein the detergent substance is based on a fatty alcohol or a fatty alcohol ethoxylate.

3. A composition as claimed in claim 1 or claim 2 wherein the cyclic siloxane is present in an amount of from 2 to 10 percent by weight based on the total weight of the composition.

4. A composition as claimed in claims 1, 2 or 3 wherein the cyclic siloxane has been incorporated as an emulsion.

5. A process for shampooing a fibrous material which consists essentially of applying to a fibrous material a detergent composition as claimed in claim 1.

6. A process as claimed in claim 5 wherein the fibrous material is human or animal hair.

* * * * *